United States Patent [19]

Barnes et al.

[11] Patent Number: 4,586,928

[45] Date of Patent: May 6, 1986

[54] PIVOTING FRANGIBLE VALVE FOR PLASTIC BAGS

[75] Inventors: Bruce E. Barnes, Kensington; William W. Dupin, Pleasant Hill; Bruce W. Kuhlemann, Hayward, all of Calif.

[73] Assignee: Miles Laboratories, Inc., Elkhart, Ind.

[21] Appl. No.: 659,064

[22] Filed: Oct. 9, 1984

[51] Int. Cl.[4] .............................................. A61B 19/00

[52] U.S. Cl. .................................... 604/408; 604/200; 604/905

[58] Field of Search ................................ 604/408–410, 604/403, 200, 262, 905; 128/DIG. 24

[56] References Cited

U.S. PATENT DOCUMENTS

| | | | |
|---|---|---|---|
| 4,270,534 | 7/1981 | Adams | 604/905 |
| 4,294,247 | 10/1981 | Carter et al. | 604/905 |
| 4,340,049 | 7/1982 | Munsch | 609/905 |
| 4,410,026 | 10/1983 | Boggs et al. | 604/262 |
| 4,435,179 | 3/1984 | Walker | 604/410 |

*Primary Examiner*—C. Fred Rosenbaum
*Assistant Examiner*—Karen Kaechele
*Attorney, Agent, or Firm*—James A. Giblin

[57] ABSTRACT

Frangible valve for a closed plastic bag system comprising an upper member having a bore and located within a port on a plastic bag and a solid lower member extending into the bag. The lower member is attached to the upper member by at least one tether and includes a bore-sealing portion attached to the upper member via a weakened portion. In use, the bore-sealing portion is separated from the upper member by external manipulation to permit fluid flow through the bore while the bore-sealing portion remains tethered to the valve. In preferred embodiments, two tethers are included on opposite sides of the bore-sealing portion and the tethered bore-sealing portion includes means for keeping it separated from the bore in a fully open position after the bore seal has been broken.

20 Claims, 7 Drawing Figures

CLOSED

OPEN

PIVOTING FRANGIBLE VALVE FOR PLASTIC BAGS

BACKGROUND OF THE INVENTION

1. Field:

This disclosure is concerned generally with plastic bags and specifically with externally manipulated frangible valves useful in closed blood bag systems.

2. Prior Art:

Closed blood bag systems include blood bags capable of holding blood and blood components which can be externally manipulated without jeopardizing the sterility of the bag contents. Although such systems may include a single blood bag and one or more attached plastic tubings, such systems may also include several bags connected via plastic tubing which serves as a conduit for transferring blood or blood components from one bag to another. Such connected bags are well known. See, for example, U.S. Pat. No. 2,702,034 to Walter and U.S. Pat. No. 3,110,308 to Bellamy. As used herein, the expression closed blood bag system includes such single bags and such connected bags, sometimes referred to as multiple blood bag systems.

When closed blood bag systems were initially used, valve systems were relatively simple. Such valves were often no more than a simple external clamp or, in later versions, a small metal bead (B-B) located within a blood bag tubing but which could be externally manipulated to fall into an attached blood bag, thereby providing flow from or to the bag through the tubing.

In later years, a more positive sealing valve was needed to preclude untimely leakage between the tubing and the bag or bags. This led to the use of positive seal transverse membranes being located within the tubing as in U.S. Pat. No. 3,110,308 to Bellamy or within a "port" attached to one end of the blood bag and into which tubing was bonded as in, for example, U.S. Pat. No. 4,195,632, to Parker et al. When sealed membranes were used, it was necessary to include a means for piercing the membrane by external manipulation of a device located within the closed system. In the Bellamy patent this was done with a small, pointed cannula located within the tubing and adjacent the transverse membrane. In the Parker et al patent, a pointed vaned spike is shown.

Although the above-described positive seal valves have been in use for sometime, they are, in many cases, difficult to use because of the external pressure required to rupture the membrane. In addition, the inclusion of a cannula or a spike within the system interfered to some extent with fluid flow after the membrane had been pierced. These shortcomings, among others, have led to the development of yet another group of blood bag valves referred to as frangible valves.

As used herein, the expression frangible valve means a valve which provides a positive seal in a closed plastic bag system and which is opened by external manipulation (without entering the closed system) of the valve, typically by breaking a portion of the valve at a weakened portion in the valve itself.

Examples of frangible valves for closed blood bag systems are shown in U.S. Pat. No. 4,007,738 to Yoshino (frangible valve located in port and tubing between bags); U.S. Pat. No. 3,654,924 to Wilson et al (frangible valve in sample pouch and having same pass through inner diameter as connecting tubing); U.S. Pat. No. 4,181,140 to Bayham et al (frangible valve with lateral vanes attached); U.S. Pat. No. 4,386,622 to Munsch (frangible valve having projecting "handles" which permit the "walking" of part of the valve after breaking, along a tubing); U.S. Pat. No. 4,270,534 to Adams (frangible valve with retention flange); U.S. Pat. No. 4,294,247 to Carter et al (re-sealing frangible valve); and U.S. Pat. No. 4,340,049 to Munsch (frangible valve with "handles"). In all of the above examples, the frangible valves are located within connecting tubing or a port or, in the case of the '924 patent, within a sample pouch. In general, such valves are still difficult to externally manipulate by hand and, in most cases, the location of the valve is such that it interferes with optimum flow of blood or blood components into or out of the blood bag. In addition, such valves or closure systems commonly contain a space above the bag top which can trap red blood cells. This typically can result in the undesirable contamination of plasma and platelet preparations with those red cells.

A blood bag known as Biopack ®P (available from Biotest Pharma, Dreieich, W. Germany) and a blood bag known as "Tuta Blood Donor Pack" (available from Tuta Laboratories (Australia) Pty., Ltd., Lane Cove, N.S.W. Australia) both include frangible valves having an upper portion located in a port and a lower portion extending into the bag and sealing a bore in the upper portion. Those valves are opened by externally manipulating the lower portion to break it at a weakened portion, thereby opening the valve for fluid flow. Unfortunately, the breakaway portion breaks completely free from the top portion, therefore allowing it to move freely within the blood or blood components which can partially or fully interfere with fluid flow. This is undesireable. Also, at the point of administration of the blood unit (typically in a hospital) the administering personnel inspecting the blood unit prior to transfusion may mistake the free floating plug as a gross clot or contaminant. In addition, when both valves are opened, the opening appears to be considerably less than the opening (inner cross section area) within the connecting tubing, thereby restricting fluid flow between the bag and connecting tubing. We have now developed a frangible valve for plastic bags which avoids the above-described shortcomings. Details are described below.

SUMMARY OF THE INVENTION

Our closed plastic bag system comprises at least one plastic bag in communication with a plastic tubing attached to a cylindrical port attached to and integral with the bag. Within the closed system is a frangible valve comprising a relative rigid material having upper and lower members. The upper member is cylindrical, has a central bore at least as large as the connecting tubing, and is adapted to be held snugly within the port via a friction or compression fit which, after conventional sterilization procedures, becomes more snug due to what is thought to be a chemical weld between the rigid valve and port, typically a polyvinyl chloride material. The lower member of the valve extends into the plastic bag and is attached to the upper member by at least one tether member and a longitudinal bore-sealing member connected to the lower portion of the upper member at a weakened area. The weakened area is adapted to be broken completely by external manual pressure through the bag walls thereby opening the bore for fluid flow. The tether member has a smaller cross section than the bore-sealing member, no weakened portion, and does not break when the bore-sealing member is broken.

In preferred embodiments, two non-breaking tethers integral with upper and lower members are provided and they are on opposite sides of the bore-sealing member. In yet further preferred embodiments, the upper portion of the bore-sealing member is adapted to pivot on the tether(s) when the seal is broken and engage the lower periphery of the upper member in a locked-open position, thereby permitting essentially unobstructed fluid flow between the bag and tubing. In other preferred embodiments, the weakened portion is generally circular and has a diameter about equal to that of the inner diameter or bore of the connecting tubing. In other applications, the tubing connects two blood bags, at least one of which is made from a polyvinyl (PVC) film, the port is made from PVC and the frangible valve is made from a relatively rigid polycarbonate material.

SPECIFIC EMBODIMENTS

The blood bags, ports and tubings of this invention are made from plastic materials well known to those skilled in the art. These materials include such well known materials as polyvinyl chloride, polyurethane and various polyolefins. In our examples the bag itself was made of PVC plasticized with a conventional plasticizer (dioctylphthalate). The port and tubing also made from PVC. Our frangible valve was made from a relatively rigid polycarbonate plastic although other plastics may be used (e.g. PVC's, polypropylene, polyesters, polyurethanes and other plastics which are medically acceptable for contact with blood and can be formed into relatively rigid pieces. The valve should be more rigid than, for example, the walls of the bag which must be pressed to break the valve.

The invention can be understood better by reference to the Figures.

Figure 1:
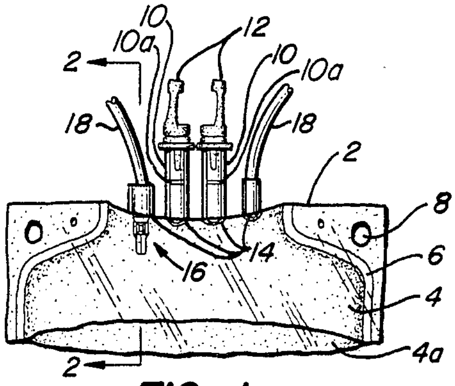
FIG. 1 illustrates the top portion of a blood bag system employing the invention.

FIG. 1 shows part of a blood bag system which includes the inventions of this disclosure. FIG. 1 illustrates the top portion of a blood bag 2 formed from two conventionally formed PVC sheets 4 and 4*a* edge sealed at 6 and including conventional openings 8 useful for bag handling (or hanging). The bag 2 includes conventional ports 14 sealed generally at the top of the bag and formed via conventional techniques using a more rigid PVC material than that used for the bag film. The illustrative middle ports include port extenders 10 terminating in removable port access caps 12 of conventional design. Between caps 12 and the top of ports 14 and within extenders 10 there are typically puncturable transverse PVC membranes 10*a* which form a seal. In use, caps 12 are removed and the interior of the bag 12 is accessible by puncturing the transverse membrane(s) with a cannula or the like. Connected via solvent weld to the remaining outer parts is conventional PVC tubing 18 which serves as a conduit for blood or blood component fluids as they enter or exit the bag 2.

The frangible valve 16 of this disclosure can be seen very generally extending fully into the left port of FIG. 1 and it is illustrated in more detail in the remaining figures.

Figure 2:
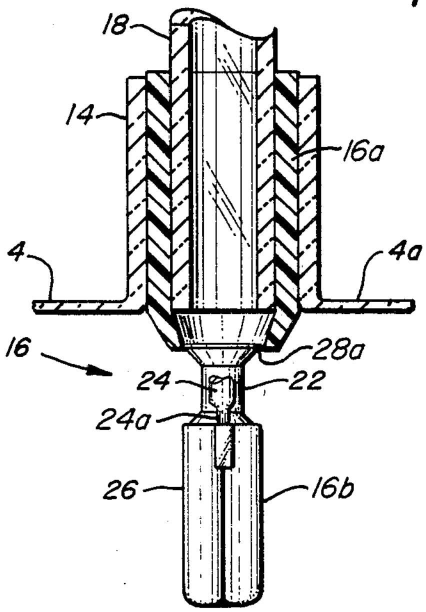
FIG. 2 illustrates a side view of the frangible valve of the invention in its closed position.

FIG. 2 illustrates in partial side view the valve 16 in a closed position between blood bag walls 4 and 4a. As can be seen, valve 16 consists of an upper member 16*a* inserted snugly (compression/weld fit) into port 14 and lower member 16*b*. In FIG. 2, conduit tubing 18 is inserted snugly (compression/weld fit) into a bore (see 20 in FIGS. 4, 5, 6 and 7) where it is solvent welded using cyclohexanone or other suitable solvent. This friction/weld type connection results in no flow restriction where tubing 18 meets upper member 16*a* of valve 16. In its closed position, bore 20 is sealed at the bottom by a top portion (see 28 of FIG. 7) at the end of an extension member 22 of overall bore-sealing member 26.

Figure 3:
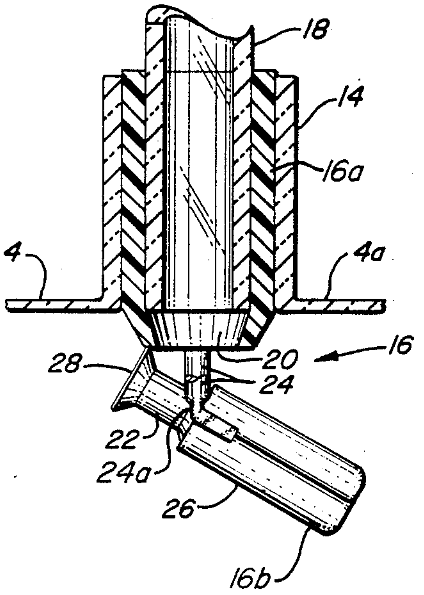
FIG. 3 illustrates a side view of the valve in its open position.

FIG. 3 illustrates in partial side view the frangible valve 16 in its locked open position. When manual pressure is applied to a blood bag sides (either 4 or 4*a*), bore-sealing member (see 26 of FIGS. 6 and 7) is separated from the upper member at a weakened portion 28*a* where top portion 28 of bore sealing member meets the bottom of upper member 16*a* of valve 16. In preferred embodiments, the bore-sealing member 26 is solid and integrally connected via top portion 22 to the bottom of the upper member 16*a* of the valve 16 via a generally weakened circular portion 28*a* (conventional for frangible plastics) in closed position and corresponding in shape to top portion 28 (FIG. 7) when the seal is open. In ideal and preferred embodiments the top 28 portion has a diameter about equal to that of the bore 20 so that when the bore is opened there is no restriction of fluid flow due to conduit constrictions. This can be accomplished by molding a weakened area 28*a* of about the diameter of the bore where top portion 22 is attached to the upper member bottom which forms the only seal at the bottom of the bore 20.

Figure 4:
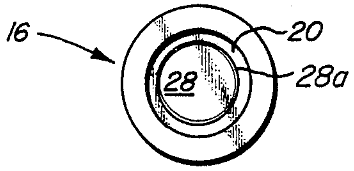
FIGS. 4 and 5 illustrate top view the frangible valve in its closed and open positions, respectively.

FIG. 4 illustrates a top view of the valve 16 showing the bore 20 into which tubing 14 (having an outer diameter about equal to the bore diameter) is inserted via friction fit and solvent welded. In one practical embodiment, the bore is about ⅜" deep and has a diameter of about 3/16".

Figure 5:
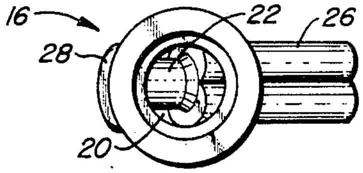
Figure 7:
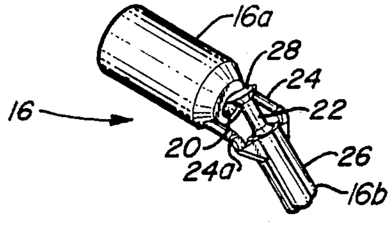

FIG. 5 illustrates a top view of the valve 16 in its open position showing how the bottom seal of bore 20 ceases to exist when bore sealing member is pressed to the right thereby applying force via extension 22 to break a circular weakened area (not shown) which defines the periphery of top portion 28 in FIG. 7.

Figure 6:
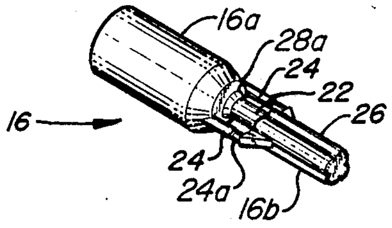
FIGS. 6 and 7 show respective perspective views of the valve in its closed and open positions.

FIGS. 6 and 7 illustrate perspective views of valve 16 in its closed and open positions showing in some detail how bore sealing member 26 is attached via two generally parallel tethers 24 to the upper member of valve 16. When the valve is closed (FIG. 6) the tethers are positioned on opposite sides of extension 22 and connected and continuous with the peripheral edge of the bottom of upper member **16*a* of valve 16 and at about the middle sides of the overall bore sealing member 26. This arrangement permits a pivoting action when bore sealing member 26 is pushed into the open position as shown in FIG. 7. In preferred embodiments, the tethers 24 are themselves slightly weakened at their lower portion 24*a* (in FIG. 7**) by being slightly thinner to facilitate pivoting at the location indicated in the drawing.

As can also be seen in FIG. 7, in the open position, the edge of top portion 28 of bore-sealing member 26 is gently snapped just past the lower peripheral edge of the bottom of the upper member **16*a* of the valve 16. This keeps the valve 16 locked in an open position after the seal is broken, thereby assuring unobstructed fluid flow through the opened bore 20, regardless of flow direction. As indicated above, top portion of 22 of bore-sealing member 26 is preferably circular and corresponds in diameter to the diameter of bore 20 to provide unrestricted fluid flow. By carefully controlling the lengths of tether arms 24 and extension 22 (about ⅛" each in one of our examples), the locking action of top portion 22 past the periphery of the bottom of upper member of valve 16 is assured. In our preferred working example, the valve 16** was molded into a single piece of polycarbonate material and the design shown in the figures could be readily sterilized in place using conventional techniques.

Although the present invention contemplates a single tether to hold the bore-sealing member after the seal is opened, in preferred embodiments two tethers are provided for added security (in case a single tether were to break) and to facilitate opening and locking open by providing an aligned plane on which manual pressure may be applied. For example, by providing two tethers 24 on opposite sides of extension 22 of bore-sealing member 26, it is easy during fabrication to align the valve 16 with the tethers in the same general plane as the edges of the generally flat (empty) blood bag. Thus aligned, the valve 16 may be opened by manual pressure applied perpendicularly on either side of the bag.

By providing tether members which are smaller in cross section area than that of the bore-sealing member 26 (or extension 22), the tethers tend to be more flexible relative to the bore sealing member 26 or extension 22 and less likely to break when the seal is broken. Further, such relative flexibility assists in keeping the top portion 22 in a locked open position once the weakened portion is broken and top portion 22 is snapped past the peripheral edge of the bottom of the upper member of the valve 16.

It can be appreciated that the above described design keeps the valve from resealing regardless of fluid flow direction, overcoming a clear shortcoming of some frangible valves which permit unrestricted flow in one direction only. The above described valve has an added advantage in use in that it requires only one bend of the lower member (extending into the bag) to open and lock open. Other devices require several tiring bends or flexes of tubing to externally manipulate and open the valve.

Given the above disclosure, it is thought numerous variations will occur to those skilled in the art. Accordingly, it is intended that the above examples should be construed as illustrative only and that the scope of the invention disclosed should be limited only by the following claims.

We claim:

1. In a closed blood bag system comprising at least one blood bag in communication with a plastic tubing attached to a cylindrical port on the bag and an externally manipulated integral frangible valve located within the closed system, the improvements comprising the valve having a cylindrical upper member fitting snugly within the port and having a bore at least as large as the tubing and a lower member extending into the bag and comprising a solid bore-sealing portion and at least one tether portion, both being attached separately to the lower portion of the upper member, the bore-sealing portion being attached to the upper member via a weakened portion adapted to permit complete separation of the bore sealing portion from the upper member by manual pressure applied to the lower member through the walls of blood bag, thereby breaking the seal and permitting essentially unobstructed fluid flow between the bag and tubing.

2. The system of claim 1 wherein the lower member includes two tether portions attached at the periphery of the lower portion of the upper member and on opposite sides of the bore sealing portion.

3. The system of claim 2 wherein the bore-sealing portion has at its upper end means for holding the bore-sealing portion away from the bore after the seal is broken.

4. The system of claim 3 wherein the upper end of the bore-sealing portion is defined by the weakened portion, is generally circular, and adapted to be kept separate from the bore by engaging the periphery of the lower portion of the upper member after the seal is broken.

5. The system of claim 2 wherein the blood bag is generally flat having two substantially parallel sides defining a plane with the two tethers being in essentially the same plane as the sides, thereby permitting the bore sealing portion of the lower member to pivot in either an upward or downward direction relative to the plane of the bag when the seal is broken.

6. The system of claim 2 wherein the bore-sealing portion includes means to keep the upper portion of the bore-sealing portion away from the bore after the seal is broken.

7. The system of claim 6 wherein the bore-sealing portion includes means for maintaining its axis at an angle of at least about 30° relative to the axis of the bore when the seal is broken.

8. The system of claim 1 wherein the tether has a smaller cross section than the bore-sealing portion.

9. The system of claim 1 wherein the blood bag comprises a polyvinyl chloride film, the frangible valve comprises a polycarbonate material, and the upper member of the valve is held in the port via an interference fit.

10. The systrm of claim 1 wherein plastic tubing connects two blood bags.

11. In a closed plastic bag system comprising at least one plastic bag in communication with a plastic tubing attached to a cylindrical port on the bag and an externally manipulated integral frangible valve located within the closed system, the improvements comprising the valve having a cylindrical upper member fitting snugly within the port and having a bore at least as large as the tubing and a lower member extending into the bag and comprising a solid bore-sealing portion and at least one tether portion, both being attached separately to the lower portion of the upper member, the bore-sealinig portion being attached to the upper member via a weakened portion adapted to permit complete separation of the bore sealing portion from the upper member by manual pressure applied to the lower member through the walls of the plastic bag, thereby breaking the seal and permitting essentially unobstructed fluid flow between the bag and tubing.

12. The system of claim 11 wherein the lower member includes two tether portions attached at the periphery of the lower portion of the upper member and on opposite sides of the bore sealing portion.

13. The system of claim 12 wherein the bore-sealing portion has at its upper end means for holding the bore-sealing portion away from the bore after the seal is broken.

14. The system of claim 13 wherein the upper end of the bore-sealing portion is defined by the weakened portion, is generally circular, and adapted to be kept separate from the bore by engaging the periphery of the lower portion of the upper member after the seal is broken.

15. The system of claim 12 wherein the plastic bag is generally flat having two substantially parallel sides defining a plane with the two tethers being in essentially the same plane as the sides, thereby permitting the bore sealing portion of the lower member to pivot in either an upward or downward direction relative to the plane of the bag when the seal is broken.

16. The system of claim 12 wherein the bore-sealing portion includes means to keep the upper portion of the bore-sealing portion away from the bore after the seal is broken.

17. The system of claim 16 wherein the bore-sealing portion includes means for maintaining its axis at an angle of at least about 30° relative to the axis of the bore when the seal is broken.

18. The system of claim 11 wherein the ether has a smaller cross section than the bore-sealing portion.

19. The system of claim 11 wherein the plastic bag comprises a polyvinyl chloride film, the frangible valve comprises a polycarbonate material, and the upper member of the valve is held in the port via an interference fit.

20. The system of claim 11 wherein plastic tubing connects two plastic bags.

* * * * *